(12) United States Patent
Lu et al.

(10) Patent No.: US 11,065,476 B2
(45) Date of Patent: Jul. 20, 2021

(54) MID-PLANE RANGE-PROBING TECHNIQUES FOR PARTICLE THERAPY

(71) Applicant: The Board of Regents of the University of Texas System, Austin, TX (US)

(72) Inventors: Weiguo Lu, Dallas, TX (US); Mingli Chen, Dallas, TX (US); Steve B Jiang, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 16/073,097

(22) PCT Filed: Jan. 26, 2017

(86) PCT No.: PCT/US2017/015082
§ 371 (c)(1),
(2) Date: Jul. 26, 2018

(87) PCT Pub. No.: WO2017/132341
PCT Pub. Date: Aug. 3, 2017

(65) Prior Publication Data
US 2019/0076673 A1 Mar. 14, 2019

Related U.S. Application Data

(60) Provisional application No. 62/287,290, filed on Jan. 26, 2016.

(51) Int. Cl.
*A61N 5/10* (2006.01)

(52) U.S. Cl.
CPC ......... *A61N 5/1075* (2013.01); *A61N 5/1031* (2013.01); *A61N 5/1077* (2013.01);
(Continued)

(58) Field of Classification Search
CPC .. A61N 5/1031; A61N 5/1075; A61N 5/1077; A61N 2005/1058; A61N 2005/1087; A61N 2005/1092
See application file for complete search history.

(56) References Cited

U.S. PATENT DOCUMENTS

| | | | | |
|---|---|---|---|---|
| 2004/0104354 A1* | 6/2004 | Haberer | ................... | G21K 5/04 250/396 ML |
| 2005/0197564 A1* | 9/2005 | Dempsey | ............... | A61B 5/055 600/411 |

(Continued)

OTHER PUBLICATIONS

International Search Report and Written Opinion Issued in Corresponding PCT Application No. PCT/US2017/015082, dated Apr. 12, 2017.

*Primary Examiner* — Sean M Luck
(74) *Attorney, Agent, or Firm* — Norton Rose Fulbright US LLP

(57) ABSTRACT

Systems, methods, and computer-readable storage media providing techniques for probing in-vivo beam ranges directly using therapeutic beams for particle therapy treatment are disclosed. In an embodiment, a configuration is determined for one or more probing spots, each spot corresponding to a planned location within an interior region of a tumor volume where a dose of radiation is to be delivered. At least one therapeutic beam is provided to the tumor volume, and one or more images may be captured to provide an indication of the range/depth of the probing spots. Providing the probing spots to the interior of the tumor volume reduces the risk that the dose is provided to sensitive tissue (e.g., because even if the dose is delivered to a location other than the planned location, the dose is likely to remain contained within the tumor volume).

17 Claims, 17 Drawing Sheets

(52) U.S. Cl.
CPC ............... *A61N 2005/1058* (2013.01); *A61N 2005/1087* (2013.01); *A61N 2005/1092* (2013.01)

(56) References Cited

U.S. PATENT DOCUMENTS

| | | | |
|---|---|---|---|
| 2008/0002811 A1* | 1/2008 | Allison | A61N 5/103 378/65 |
| 2008/0049896 A1* | 2/2008 | Kuduvalli | A61N 5/1049 378/65 |
| 2009/0314960 A1 | 12/2009 | Balakin | |
| 2010/0280374 A1* | 11/2010 | Roberts | A61N 5/1001 600/439 |
| 2010/0301235 A1* | 12/2010 | Bert | A61N 5/103 250/492.3 |
| 2011/0108737 A1* | 5/2011 | Pu | A61N 5/1043 250/398 |
| 2011/0122997 A1* | 5/2011 | Lu | A61N 5/1031 378/65 |
| 2011/0182806 A1 | 7/2011 | Schulte et al. | |
| 2012/0041685 A1* | 2/2012 | Ding | A61B 6/032 702/19 |
| 2012/0165652 A1* | 6/2012 | Dempsey | A61N 5/1045 600/411 |
| 2012/0280135 A1* | 11/2012 | Bal | A61B 5/0033 250/395 |
| 2012/0313002 A1* | 12/2012 | Ikeda | A61N 5/1043 250/393 |
| 2013/0102830 A1* | 4/2013 | Otto | A61N 5/00 600/1 |
| 2013/0137916 A1 | 5/2013 | Goer | |
| 2013/0231516 A1* | 9/2013 | Loo | A61N 5/1065 600/1 |
| 2015/0087882 A1* | 3/2015 | Pausch | A61N 5/1067 600/1 |
| 2015/0099917 A1* | 4/2015 | Bula | A61N 5/1044 600/1 |
| 2015/0231411 A1* | 8/2015 | O'Neal, III | H05H 13/04 600/1 |
| 2015/0238780 A1* | 8/2015 | Nishimura | A61N 5/1043 600/2 |
| 2015/0297917 A1* | 10/2015 | Beekman | A61N 5/1043 600/1 |
| 2015/0343238 A1* | 12/2015 | Balakin | A61N 5/1082 600/1 |
| 2015/0360057 A1* | 12/2015 | Balakin | A61N 5/1081 600/1 |

\* cited by examiner

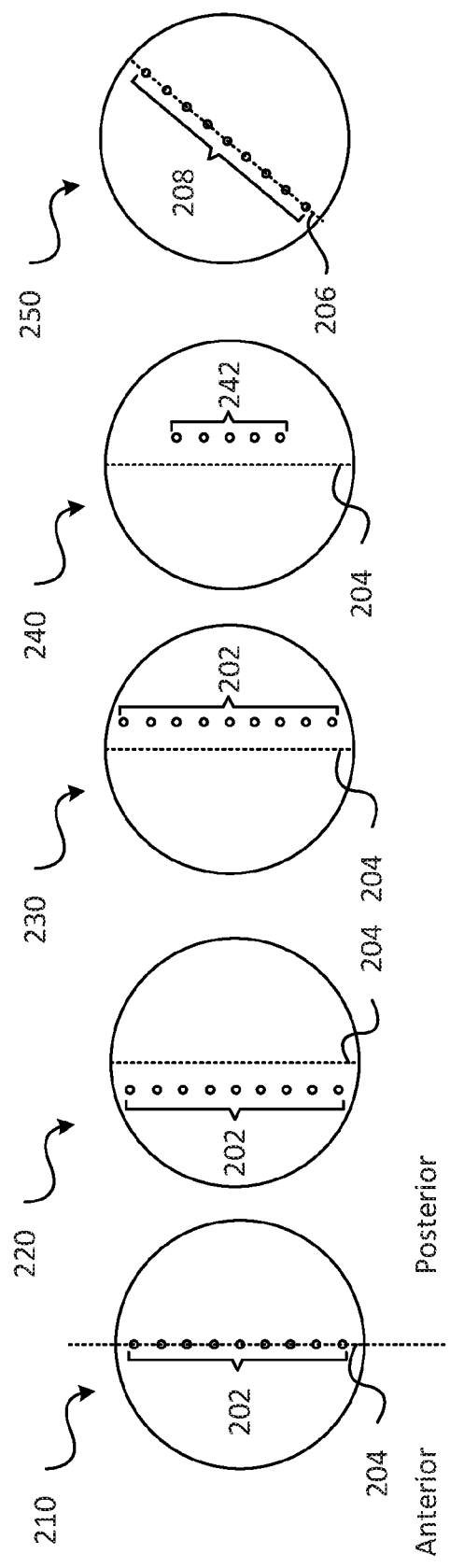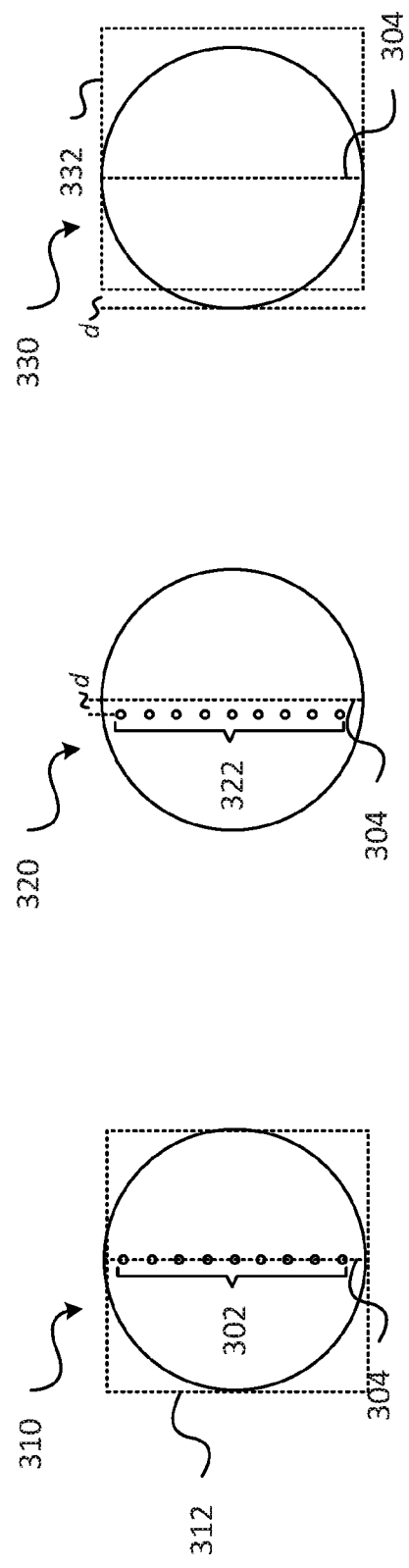
FIG. 2
FIG. 3

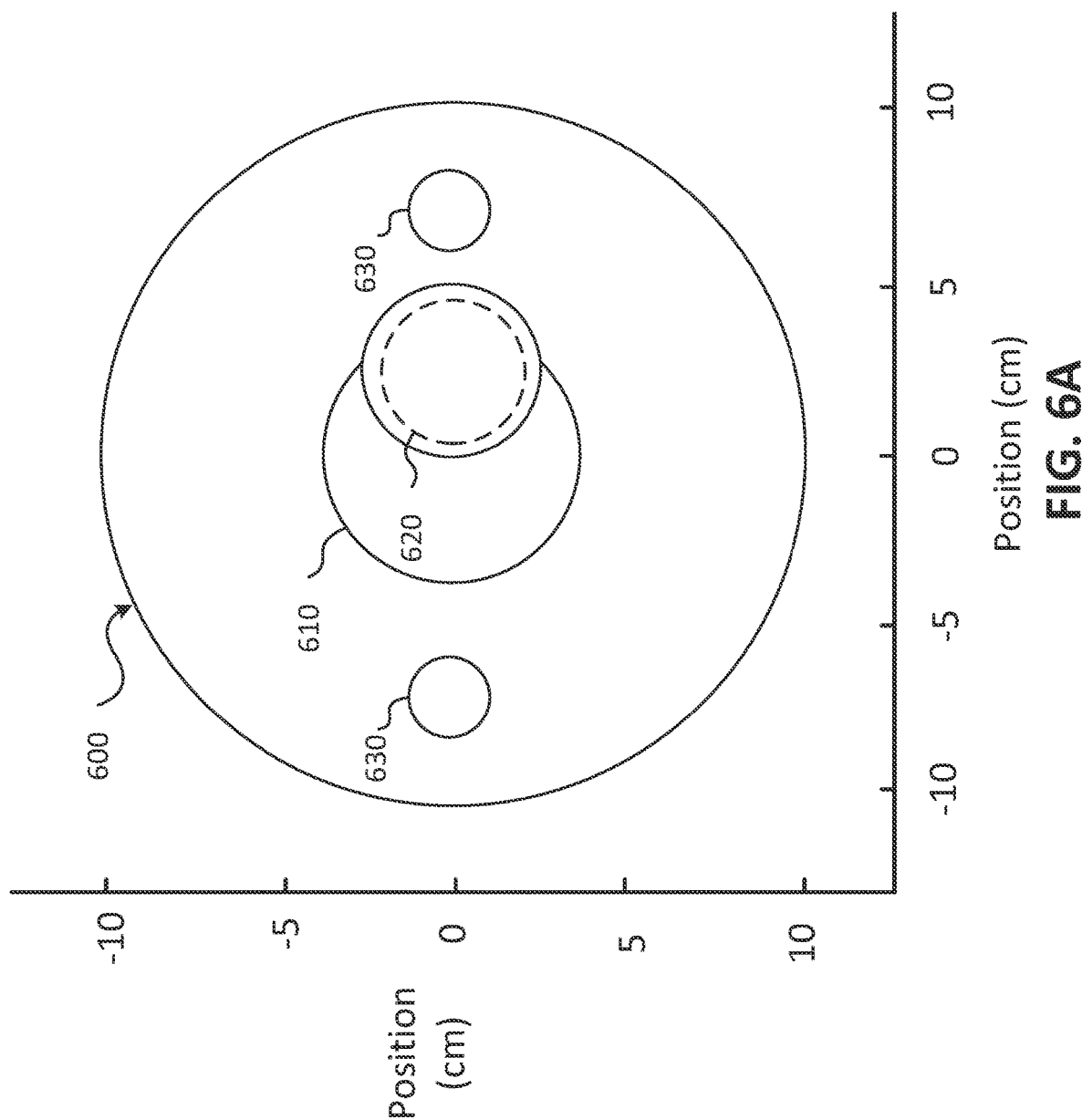

MID-PLANE RANGE-PROBING TECHNIQUES FOR PARTICLE THERAPY

CROSS-REFERENCE TO RELATED APPLICATIONS

This application is a national phase application under 35 U.S.C. § 371 of International Application No. PCT/US2017/015082, filed Jan. 26, 2017 which claims the benefit of priority of U.S. Provisional Application No. 62/287,290 filed Jan. 26, 2016 each of which is hereby incorporated by reference in its entirety.

FIELD OF INVENTION

The present disclosure is generally related to particle therapy, and more particularly to range-probing techniques for determining beam ranges used in particle therapy.

BACKGROUND

Particle therapy refers to the use of proton beams and/or heavy ion beams (e.g., carbon ion beams, helium ion beams, argon ion beams, etc.) to treat tumors. Particle therapy offers several advantages over other radiotherapy techniques (e.g., x-ray radiotherapy techniques). One of the more notable advantages is that particle therapy provides more precise delivery of radiation to the tumor volume than other radiotherapy techniques, which allows the dose to be delivered to the tumor with a reduced risk that the dose will be delivered to sensitive tissues and organs adjacent to or surrounding the tumor.

In particle therapy, a treatment plan consists of one or more therapeutic beams. Each therapeutic beam consists of one or more layers of spots. Each layer of spots may have the same energy with various intensities. Additionally, each layer of spots will deliver a radiation dose to various depths of the tumor, depending on the configuration of the beam path. Careful planning is often performed prior to performing particle therapy because the position at which a particle therapy beam is delivered is sensitive to, and may be altered by, several factors. For example, filling of a naso-cavity or appearance of bone structures in the path of the beam may shorten the beams delivery depth, causing the dose provided by the beam to be delivered at a location shallower than a planned location. As another example, when an air pocket is present in the beam path, the dose may be delivered at a location that is deeper than intended. As yet a further example, the patient may undergo physical changes (e.g., lose weight, etc.) that alter the patient's anatomy, and those changes may further alter the location at which the dose is provided relative to a planned position. It is estimated that a 1 centimeter (cm) section of bone or air pocket encountered in the beam path may shift the dose 1 cm upstream or downstream, respectively. Thus, the ability to perform in-vivo range verification is critical in particle therapy.

SUMMARY

Systems, methods, and computer-readable storage media providing techniques for probing beam ranges used for particle therapy treatment are disclosed. The range-probing techniques described in connection with one or more of the embodiments disclosed herein may provide a more accurate in-vivo determination of the delivery location of a dose (e.g., a dose of radiation) provided by a beam used to perform particle therapy treatment of a tumor. Simultaneously, the range-probing techniques of embodiments disclosed herein may reduce the likelihood that the beam will provide the dose to sensitive tissue in the vicinity of the tumor volume.

In an embodiment, a range-probing technique may include determining a configuration of one or more probing spots. In an embodiment, the one or more probing spots may be selected from a planned therapeutic beam and/or a treatment plan. Each of the one or more probing spots may correspond to a planned location within an interior region of a tumor volume where a dose of radiation is to be delivered by at least one therapeutic beam. In an embodiment, the dose of radiation delivered by at least one therapeutic beam may have a strength that corresponds to at least a partial therapeutic dose. In an embodiment, the probing spots provided in accordance with the present disclosure may be provided by an at least partially therapeutic beam (e.g., a beam providing a dose of approximately 2-20 Gy or greater). After the configuration has been determined, at least one therapeutic beam may be provided to the tumor volume in accordance with the configuration.

During the providing of the at least one therapeutic beam to the tumor volume, one or more images may be captured. The one or more images may provide data representative of a delivery location of one or more spots delivered by the at least one therapeutic beam within the tumor volume. In an embodiment, one or more Bragg peaks may be determined from, or included in, the image data. The one or more images may provide an indication of the range or depth of the spots corresponding to where the dose(s) was delivered within the tumor volume by the one or more beams. Because the spots were generated using an at least partially therapeutic beam (e.g., a dose that is two-orders higher than a conventional imaging dose, which provides a signal strength that is two-orders higher than a signal strength provided by the conventional imaging dose), the spots may be more easily observed from the one or more images, allowing for accurate range determinations. Additionally, because the spots were provided to the interior of the tumor volume, rather than an interior region proximate an exterior surface of the tumor volume, the risk that the dose is provided to sensitive tissue (e.g., organs, etc.) within the vicinity of the tumor may be reduced or eliminated (e.g., because even if the dose is delivered to a location other than the planned location, the dose may be highly likely to remain contained within the tumor volume). The observed locations of the spots may be compared to the planned locations of the spots to perform range calculations. Additional advantages and features of the disclosed embodiments are provided in the accompanying Figures and the Detailed Description which follows.

The term "coupled" is defined as connected, although not necessarily directly, and not necessarily mechanically. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially" and "approximately" may be substituted with "within [a percentage] of" what is specified, where the percentage includes 0.1, 1, 5, and 10%.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 2 is a block diagram illustrating various embodiments of configurations for probing spots for use in performing range-probing of beams used for particle therapy treatment;

FIG. 3 is a block diagram illustrating an embodiment of a technique for performing range-probing of one or more beams used for particle therapy treatment;

FIG. 6A is a diagram illustrating a second exemplary phantom;

DETAILED DESCRIPTION

Figure 1:
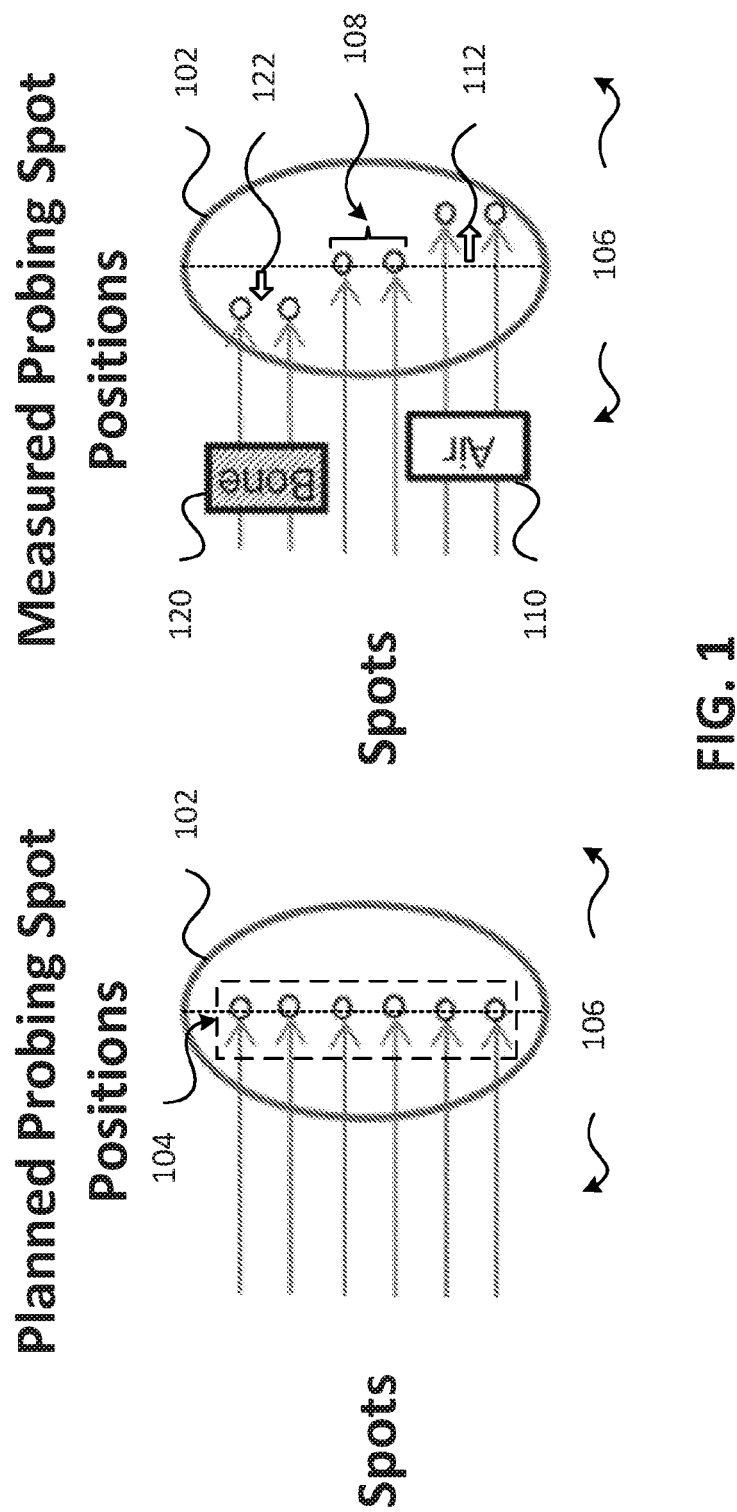
FIG. 1 is a block diagram illustrating a technique for probing beam ranges used for particle therapy treatment.

Referring to FIG. 1, a block diagram illustrating a technique for probing beam ranges used for particle therapy treatment is shown. On the left-hand side of FIG. 1, a diagram illustrating planned spot probing of a tumor 102 is shown, and on the right-hand side of FIG. 1, a diagram illustrating actual spot probing of the tumor 102 is shown. As shown in FIG. 1, the tumor 102 may be surrounded by tissue 106.

In an embodiment, the tissue 106 may include sensitive tissue, such as organs, which may be damaged by delivery of a dose of radiation (e.g., a dose intended for delivery to the tumor 102). To reduce or eliminate the likelihood that a portion of the dose is delivered to the tissue 106, one or more probing spots within an interior of the tumor 102's volume, as indicated by the box 104, may be used as probing spots. It is noted that although FIG. 1 illustrates the probing spots being located approximately within the center of the interior of the tumor 102's volume, embodiments of the present disclosure should not be so limited.

For example, and referring to FIG. 2, a block diagram illustrating various embodiments of configurations for probing spots for use in performing range-probing in particle therapy treatment are shown. In an embodiment of a first exemplary configuration 210, a plurality of spots 202 are shown positioned along a mid-line 204 located at approximately the center of the tumor's volume. At 220, a second illustrative embodiment shows the plurality of spots 202 arranged within the interior of the tumor's volume on a first side (e.g., an anterior side) of the mid-line 204, and, at 230, a third illustrative embodiment shows the plurality of spots 202 arranged within the interior of the tumor's volume on a second side (e.g., a posterior side) of the mid-line 204. It is noted that although the two sides of the mid-line 204 are referenced as an anterior side and a posterior side, such references are provided for purposes of illustration, rather than by way of limitation. At 240, a fourth illustrative embodiment is shown and illustrates that the number of spots that are planned may vary depending on the desired treatment plan, or for other considerations. In an embodiment, the number of spots that are used for range-probing may be as few as 1 spot, or may include layers of spots of the same energy or multiple layers of spots. The number of spots may be determined based on the size of the tumor to be treated, an angle at which the therapeutic beam is to deliver the dose to the tumor volume, other factors, or a combination thereof.

In some embodiments, multiple sets of probing beams may be determined/configured. For example, when a treatment plan calls for the at least one therapeutic beam to be provided to the tumor at various angles (e.g., due to concerns with respect to preventing damage to the tissue surrounding the tumor, or for other reasons), one or more probing-spots from each planned therapeutic beam may be determined/configured for each angle. Thus, for example, at 250, a fifth illustrative embodiment is shown and illustrates that one or more spots 208 may be used as probing beams along another interior region 206 within the tumor's volume. At least a portion of the other interior region 206 may overlap with a region identified by the mid-line 204, and other portions of the other interior region 206 may be distinct from region identified by the mid-line 204. For example, the embodiment illustrated at 210 may correspond to a probing beam configuration for a first angle of the therapeutic beam, and the embodiment illustrated at 250 may correspond to a probing beam configuration for a second angle of the therapeutic beam, where the first and second angles are different.

Referring back to FIG. 1, each of the one or more probing beams may correspond to a planned location within an interior region of the tumor 102's volume where a dose of radiation is to be delivered by at least one therapeutic beam. In an embodiment, the configuration may be determined based on one or more images of the tumor 102 and the area surrounding the tumor 102. The one or more images used to determine the configuration of the probing beams may correspond to images generated using a Positron emission tomography (PET) technique, a prompt Gamma imaging technique, another imaging technique, or a combination thereof. In an embodiment, the dose of radiation (e.g., each of the spots) delivered by the at least one therapeutic beam may have a strength corresponding to at least a partial therapeutic dose. In an embodiment, the dose provided by the therapeutic beam may have a strength that is approximately two orders of magnitude higher than a conventional dose provided by a conventional imaging beam. For example, a conventional imaging beam may have a dose of approximately 1-10 cGy or less, and the therapeutic beam of some embodiments may provide a dose of approximately 2-20 Gy or greater. In an embodiment, the therapeutic beam may be a proton beam. In an additional or alternative embodiment, the therapeutic beam may be a heavy ion beam. In an embodiment, the heavy ion beam may be formed using carbon ions, helium ions, argon ions, or another suitable ion.

After planning is completed, and the configurations of the one or more probing beams have been determined, at least one probing beam may be provided to the tumor volume in accordance with the configuration. During the providing of that at least one probing beam to the tumor volume, one or more images may be captured. In an embodiment, the one or more images provide data representative of a delivery location of one or more spots delivered by the at least one therapeutic beam within the tumor volume. The one or more images may be captured using positron emission tomography (PET), or another suitable imaging technology.

The one or more images captured during the delivery may be used to determine a delivery location for each of the one or more probing spots. The delivery location for each of the one or more probing spots may be compared to the planned location for each of the one or more probing spots, and, for each of the one or more probing spots, a difference between the delivery location and the planned location may be determined based on the comparing. For example, and referring to FIG. 3, a block diagram illustrating an embodiment of a technique for performing range-probing of one or more beams used for particle therapy treatment is shown. As shown at 310, a treatment plan 312 may be determined for treating a tumor, and, prior to treating the tumor according to the treatment plan 312, probing spots 302 may be configured along an interior region 304 of the tumor. It is noted that the treatment plan 312 is illustrated as a square for purposes of illustration only, and is not intended to indicate the actual area to which a dose of radiation is to be provided. At 320, a therapeutic beam providing at least a partial therapeutic dose may be provided to the tumor, resulting in probing spots 322. It is noted that alignment may be performed prior to performing range-probing in accordance with the embodiments disclosed herein. As shown at 320, the delivery location of the probing spots 322 diverges from the planned location of the probing spots 302 by a distance d. It is noted that although d is shown as a 2 dimensional distance, the difference d between the planned locations for the probing spots 302, and the delivery location for the probing spots 322 may differ in more than two dimensions. It is further noted that the difference between one or more of the probing spots 302 and their corresponding delivered probing spots 322 may not be uniform (e.g., some delivered spots may have a large d relative the corresponding probing spot than others). Additional details regarding factors that may affect the distance d are described with reference to FIG. 1, below. Adjustments may be made to the treatment plan 312 based on the observed distance d for each of the delivered probing spots 322. For example, at 330, it is shown that the treatment plan may be shifted by the amount d such that the treatment plan will more effectively deliver the treatment dose to the desired locations within the tumor volume, without delivering the dose to tissue surrounding the tumor. However, it is noted that in some embodiments, only a portion of the treatment plan 312 may be adjusted based on d, or portions of the treatment plan may be adjusted in different directions. Exemplary embodiments of adjusting a treatment plan are described in more detail below.

Referring back to FIG. 1, structures, such as bones and air pockets, are often present within a beam path during particle therapy treatments. Thus, on the right-hand side of FIG. 1 a bone 120 and an air pocket 110 are shown. Such structures may alter the range of the therapeutic beam, and alter the delivery location of a dose provided by the therapeutic beam. For example, as illustrated on the right hand side of FIG. 1, the depth of spots corresponding to one or more beams or beam portions passing through the bone 120 may be more shallow (e.g., closer to the origin of the beam(s)) than the planned location, as indicated by the arrow 122, and the depth of spots corresponding to one or more beams or beam portions passing through the air pocket 110 may be deeper (e.g., further from the origin of the beam(s)) than the planned location, as indicated by the arrow 112. However, as illustrated in FIG. 1, by planning the probing spots at the interior region of the tumor 102's volume, the tissue 106 may not be exposed to the dose during probing. Thus, configuring the probing spots along the interior region of the tumor 102 may prevent sensitive tissue (e.g., the tissue 106) from being damaged by exposure to the dose delivered by the therapeutic beam used to provide the probing spots. In some embodiments, the depth of probing spots corresponding to one or more beams or beam portions that do not pass through the air pocket 110 and/or the bone 120 may be approximately the same as the planned location, as indicated at 108. When additional probing spot configurations are determined, such as for different angles of providing the dose to the tumor 102, additional shifts of probing spots may be observed. Such additional shifts and delivery locations may be further used to modify a treatment plan (e.g., the treatment plan 312 of FIG. 3) based on the determined differences between the delivery location and planned location for each of the one or more additional probing spots. Further, in some embodiments, because the probing spots are provided as therapeutic or at least partially therapeutic doses, they may be accounted for when implementing the treatment plan following any adjustments made based on the probing, as described in more detail below.

Figure 4:
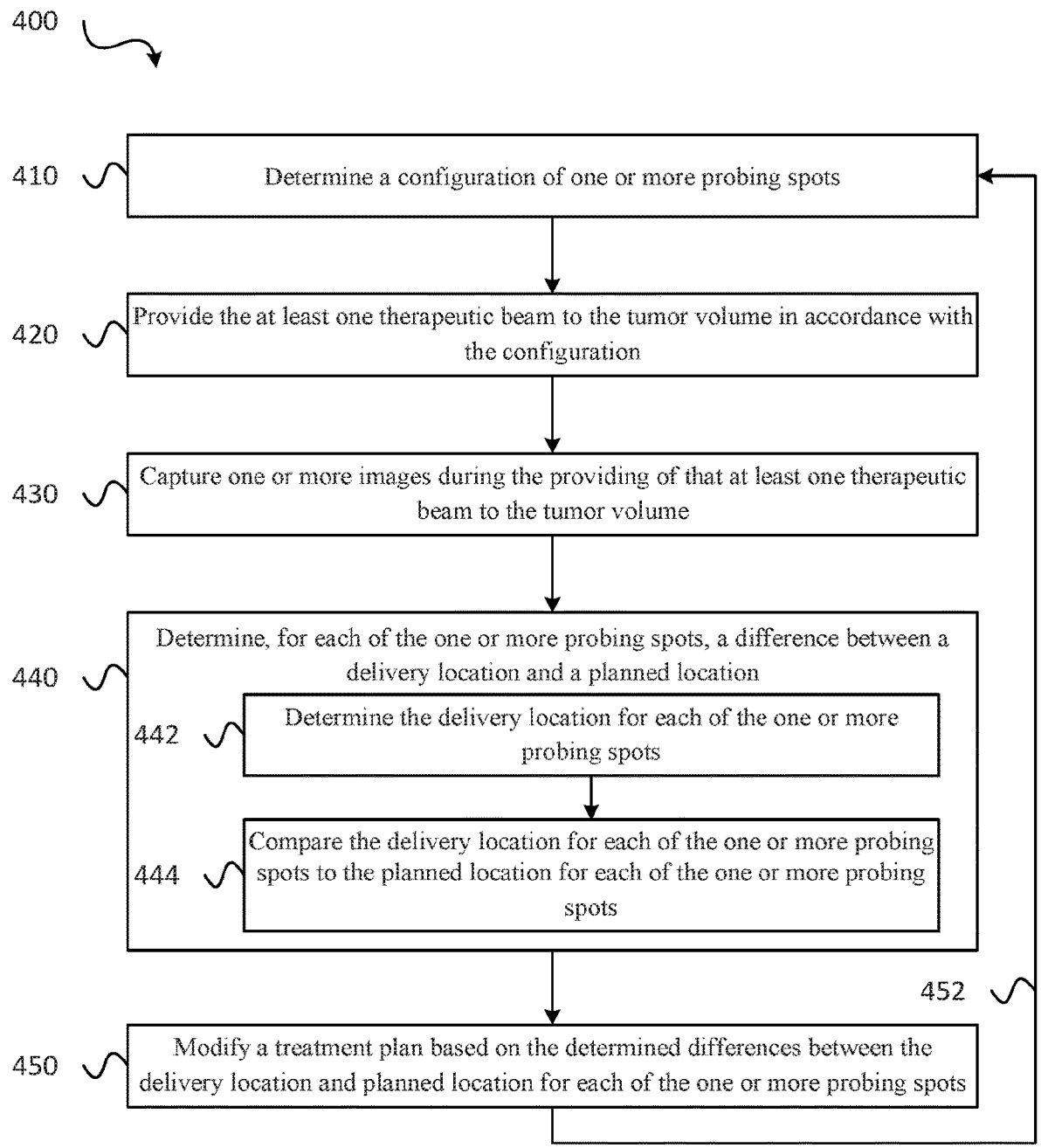
FIG. 4 is a flow diagram of an embodiment of a method for probing beam ranges used for particle therapy treatment.

Referring to FIG. 4, a flow diagram of an embodiment of a method for probing beam ranges used for particle therapy treatment is shown as a method 400. In an embodiment, the method 400 may be stored at a memory as instructions that, when executed by a processor, cause the processor to perform operations for probing beam ranges used for particle therapy treatment. At 410, the method 400 includes determining a configuration of one or more probing spots. In an embodiment, a treatment plan may define one or more spots where a dose of radiation is to be delivered to a tumor volume during particle therapy treatment, and configuring the probing spots may include selecting spots defined by the treatment plant as probing spots. In accordance with at least embodiments of the present disclosure, the spots defined by the treatment plan that are selected as probing spots may reside near a mid-plane (e.g., mid-layer, or more generally, inside the tumor but away from the tumor boundary). In an embodiment, each of the one or more probing spots may correspond to a planned location within an interior region of a tumor volume where a dose of radiation is to be delivered by at least one therapeutic beam (e.g., the therapeutic beam described in connection with FIGS. 1-3). In an embodiment, the dose of radiation delivered by at least one therapeutic beam may have a strength corresponding to at least a partial therapeutic dose (e.g., a dose as described with reference to FIGS. 1-3). Using planned mid-plane spots as probing beams in accordance with at least some of the present embodiments may provide more image contrast (e.g., because of the higher dose) compared with using low-dose imaging beams. Because the probing beam dose is part of the treatment plan, the dose provided to the tumor volume by the probing beam/spot may be accounted for in plan modification, if necessary, and no extra radiation is delivered to the patient by the probing beam.

At 420, the method 400 may include providing the at least one therapeutic beam to the tumor volume in accordance with the configuration, and, at 430, capturing one or more images during the providing of the at least one therapeutic beam to the tumor volume. In an embodiment, the one or more images may provide data representative of a delivery location of one or more probing spots (e.g., doses) delivered by the at least one therapeutic beam within the tumor volume. At 440, the method 400 may include determining, for each of the one or more probing spots, a difference between a delivery location and the planned location. In an embodiment, determining the difference may include, at 442, determining the delivery location for each of the one or more probing spots, and, at 444, comparing the delivery location for each of the one or more spots to the planned location for each of the one or more probing spots. In an embodiment, the delivery location may be determined, for each of the one or more probing spots, based on the one or more images captured during the providing of the at least one therapeutic beam to the tumor.

At 450, the method 400 may include modifying a treatment plan based on the determined differences between the delivery location and planned location for each of the one or more probing spots. The modifications may include modifying an angle of delivery for one or more spots of treatment plan, modifying a planned depth or location for one or more of the spots of treatment plan, increasing or decreasing the number of spots used to deliver a final therapeutic dose to the tumor, another type of modification, or a combination thereof. In an embodiment, additional configurations for one or more additional probing spots may be determined, such as when multiple beam angles are to be used to treat the tumor. In such instances, the method 400 may include, at 452, determining additional configurations for one or more additional probing spots, and repeating one or more steps of the method 400 to analyze the results of the additional probing spots (e.g., based on probing using the steps 420-440), and the results of the additional probing may be used to further modify the treatment plan.

In some embodiments, modifying the treatment plan, at 450, may comprise range modification, treatment plan re-optimization, or a combination thereof. In some embodiments, a treatment plan I or intensity map for scanned ion beam therapy may be parameterized by the following parameters (E, x, y, $\varphi$), where E denotes the beam energy and (x, y) denote the coordinates on the fluence plane for the beam angle $\varphi$. However, for convenience, during simulation of some embodiments of the present probing techniques, the intensity map I was parameterized using the Bragg peak position R measured using water equivalent path length (WEPL) instead of the beam energy E. This was possible because the Bragg peak position and the beam energy have a one-to-one correspondence.

For range modification, suppose that there is a shift, $\Delta R \neq 0$ measured in WEPL, between the planned mid-range spot and the probed spot, where a positive difference $\Delta R > 0$ indicates that the probed spot is further from the source. A correction strategy according to some embodiments may apply range shifting to the plan. For example, let $I_0$ denote the original plan. Then the new intensity defined at (R, x, y, $\varphi$) should be $I_0(R+\Delta R, x, y, \varphi)$, which may be expressed as:

$$I_1(R,x,y,\varphi)=I_0(R+\Delta R,x,y,\varphi) \quad \text{Eq. (1)}$$

This range correction is based on the assumption that the WEPL in the target does not change.

To account for the probing beam dose, the probing beam intensity delivered to the planned mid-range spot ($R_0$, x, y, $\varphi$) may be subtracted from the shifted intensity, which may be expressed as:

$$I_1(R_0,x,y,\varphi)=(I_0(R_0+\Delta R,x,y,\varphi)-I_0(R_0,x,y,\varphi))_+ \quad \text{Eq. (2)}$$

Alternatively or additionally, the plan may be re-optimized using range-shifted beamlets based on the range difference identified through probing beams. For example, let $B_{R,x,y,\varphi}$ denote the original beamlet indexed by (R, x, y, $\varphi$) as described above. The beamlet $B_{R,x,y,\varphi}$ is a three dimensional distribution parametrized by spatial coordinates ($p_x$, $p_y$, $p_z$): $B_{R,x,y,\varphi}$ ($p_x$, $p_y$, $p_z$), where positive $p_z$ is in the beam direction $\varphi$. The shifted beamlet $B^*_{R,x,y,\varphi}$ may be expressed as:

$$B^*_{R,x,y,\varphi}(p_x,p_y,p_z)=B_{R,x,y,\varphi}(p_x,p_y,p_z-\Delta R) \quad \text{Eq. (3)}$$

In embodiments, the range shift can be compensated via online plan modification, which may formulated as a 1D optimization problem. For 1 D optimization, different spots (non-zero intensity) from those of the original plan may be needed. This problem may be addressed by including spots before and after the tumor on the probe beam path, during plan optimization. The additional spots may have zero intensity in the original plan but may be needed for online re-optimization. The spots along the probing beam path indicate that intensity is re-optimized to account for range shift. The Bragg peak position (spot) is indexed from 1 to K. The probing beam uses the planned mid-range spot, indexed by k, and may shift due to patient anatomical variations on the treatment day. Let p denote the position of the planned mid-range spot, and p' denote that of the online delivered spot. Let s denote the shift s=p'−p. The shift may be used to update beamlets and re-optimize fluence for beamlets along the line of the probe beam. Re-optimization may be formulated as follows:

$$\min_{\{w_k\}} \|\Sigma_{k=1} w_k B_k(x-s) + w_{\bar{k}}^0 B_{\bar{k}}(x-s) - d^0(x)\|^2, \quad (4)$$

where $\{B_k\}$ are pre-calculated beamlets, k is a beamlet index, K is the total number of beamlets along the probing spot direction, $\bar{k}$ is the index of the planned mid-range beamlet, $\{w_k\}$ are the fluences to be optimized, $w_{\bar{k}}^0$ is the intensity of the planned mid-range beamlet, $d^0$ is the planned dose, x is the positional variable along the line of the probe beam, and the norm $\| \; \|$ denotes the $L_2$-norm, where the planned dose may calculated from the planned fluence according to:

$$d^0(x) = \Sigma_{k \in K} w_k^0 B_k(x), \quad \text{Eq. (5).}$$

Figure 5A:
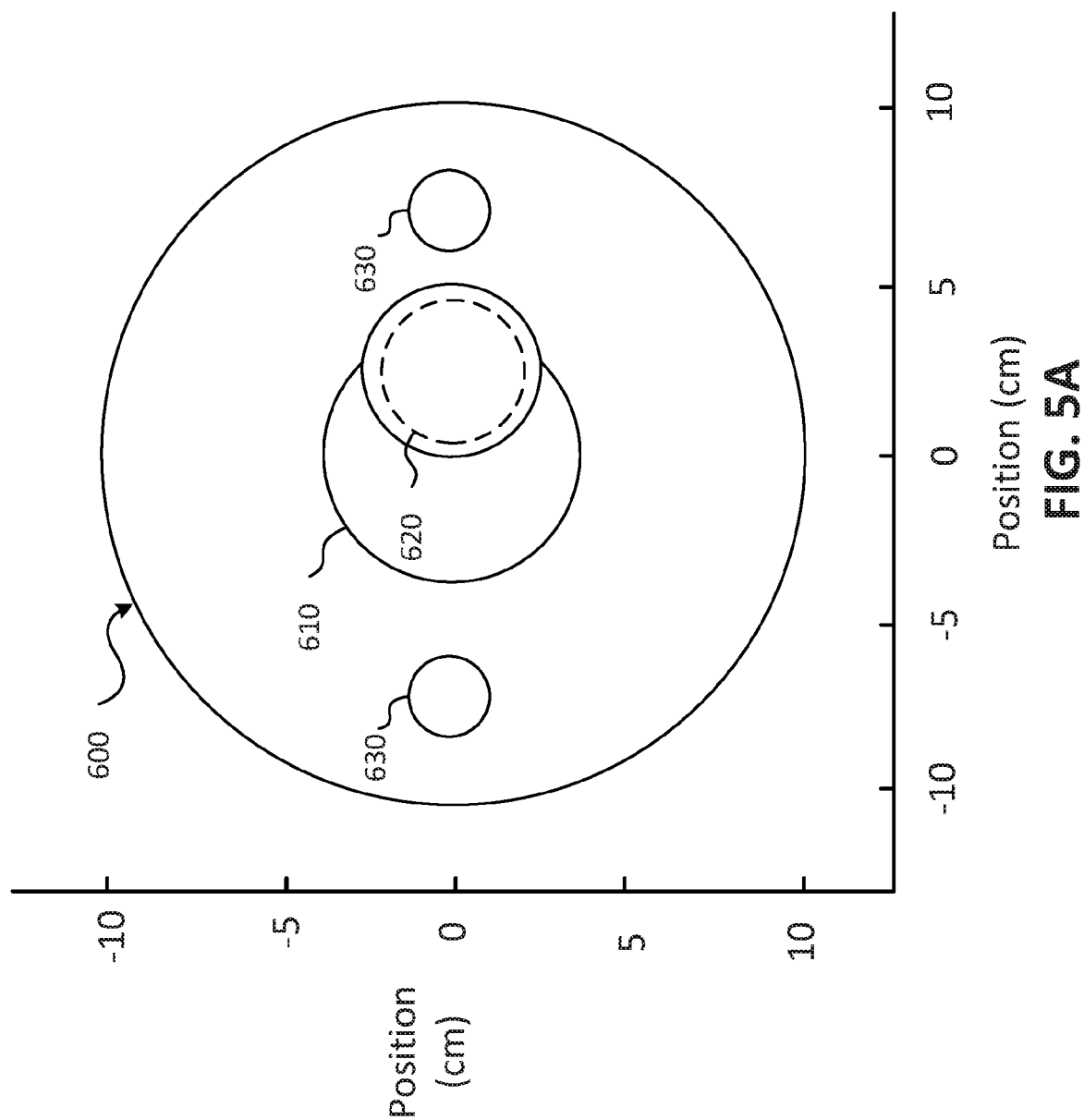
FIG. 5A is a diagram illustrating a first exemplary phantom.

Using the aforementioned techniques, a treatment plan may be determined that accounts for any shifts in the delivery location of a dose provided by a therapeutic beam that may be caused by structures (e.g., bones, air pockets, etc.) in the body of the patient. Additionally, because the probing beams provided in accordance with some embodiments are less likely to deliver a dose outside of the tumor volume due to the planned mid-range probing, sensitive tissues proximate the tumor are less likely to be damaged during the probing due to shift of the probing beams. Additionally, as described above, the modified treatment plan may account for the therapeutic or at least partially therapeutic doses provided by the probing beams, thereby prevent delivery of a dose that is in excess of an intended dose. To analyze aspects of at least some of the present embodiments for applying mid-range probing beams, two reference phantoms were prepared. A first phantom 500 was a circular phantom with a crescent target 510 at the center embracing a circular organ at risk (OAR) 520 and two symmetrically-located air pockets 530, as shown at FIG. 5A. The second phantom was similar to the first phantom, except that the assignments of the target and OAR are switched. For example, in FIG. 6A, the second phantom is shown and includes a circular phantom 600 with a crescent OAR 610 at the center embracing a circular target 620 and two symmetrically-located air pockets 530 A treatment plan was optimized for each reference phantom, and the results were used to illustrate the selection of the probing beams.

A brain CT case was also studied, as described below with reference to FIGS. 7A-7C, and a treatment plan was optimized, and the mid-range probing beams were delivered to two simulated online scenarios, one with an air pocket and the other with a bony structure on the beam path. Each online scenario impacted the beam ranges. Following the probing beam, we measured the online beam ranges and applied range correction.

Figure 5B:
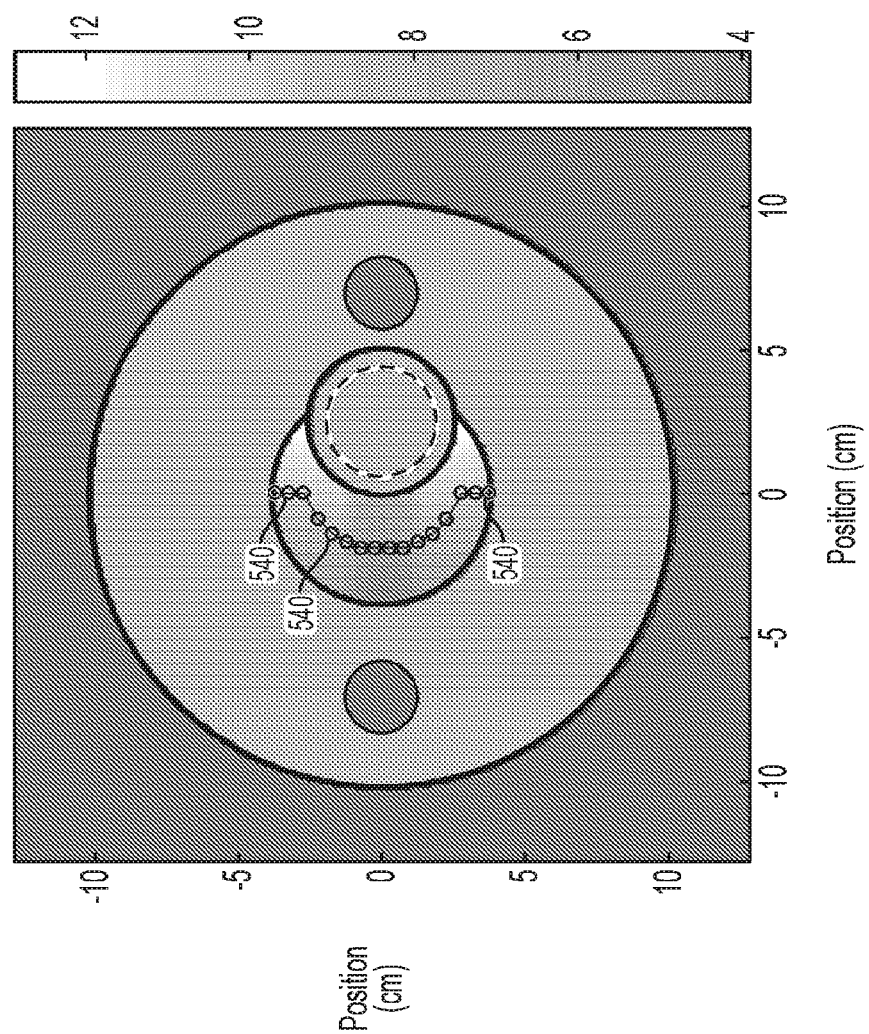
FIG. 5B is a diagram illustrating aspects of an optimized treatment plan.
Figure 5C:
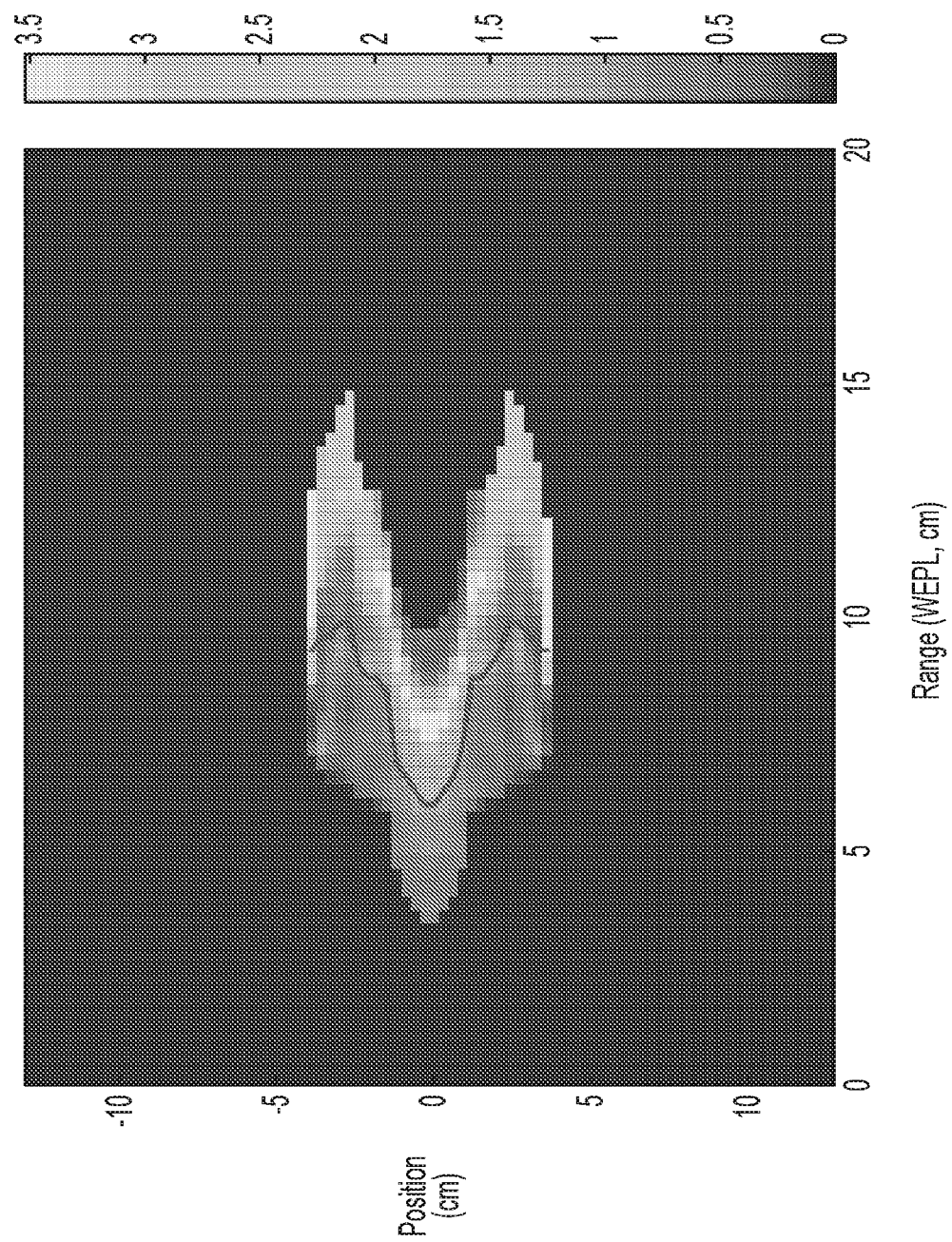
FIG. 5C is another diagram illustrating aspects of an optimized treatment plan.
Figure 5D:
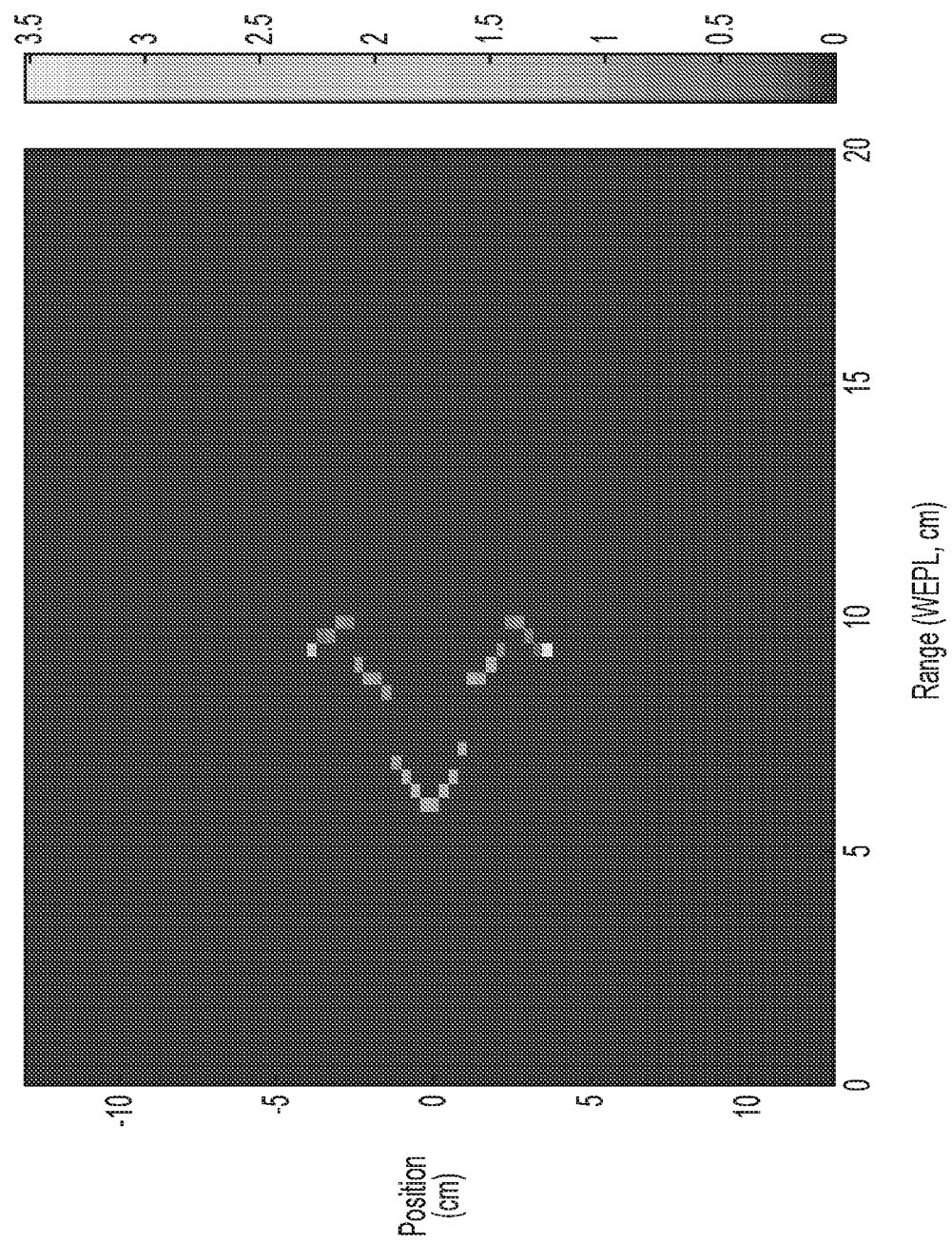
FIG. 5D is another diagram illustrating aspects of an optimized treatment plan.
Figure 6B:
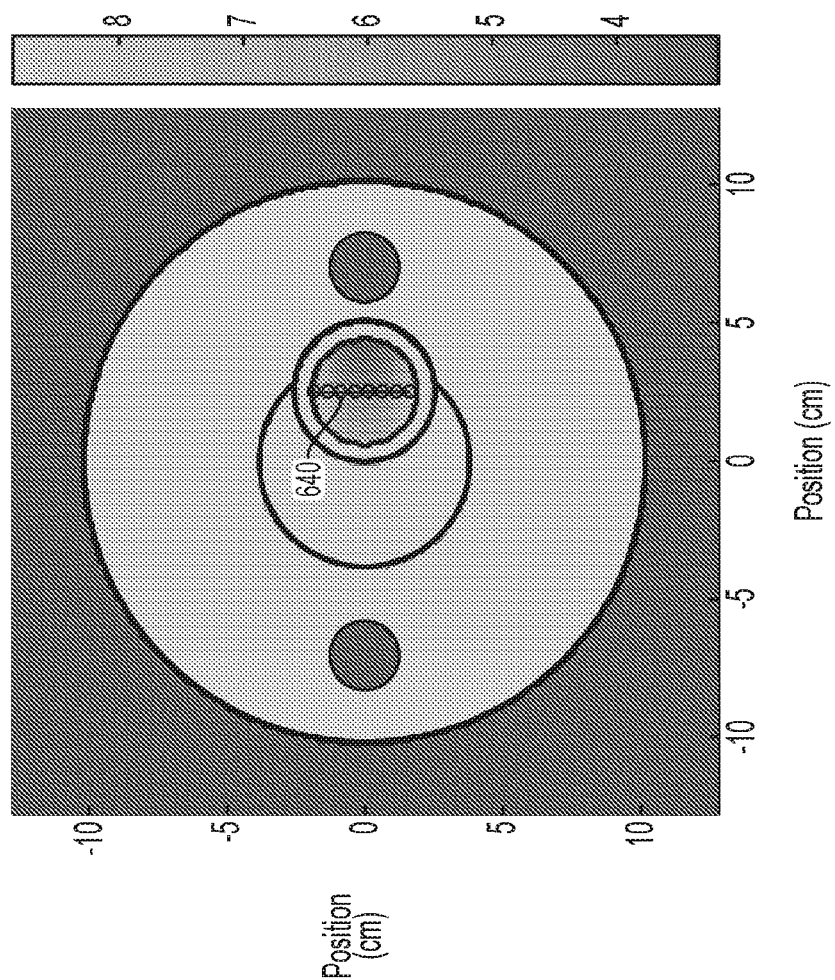
FIG. 6B is a diagram illustrating aspects of an optimized treatment plan.
Figure 6C:
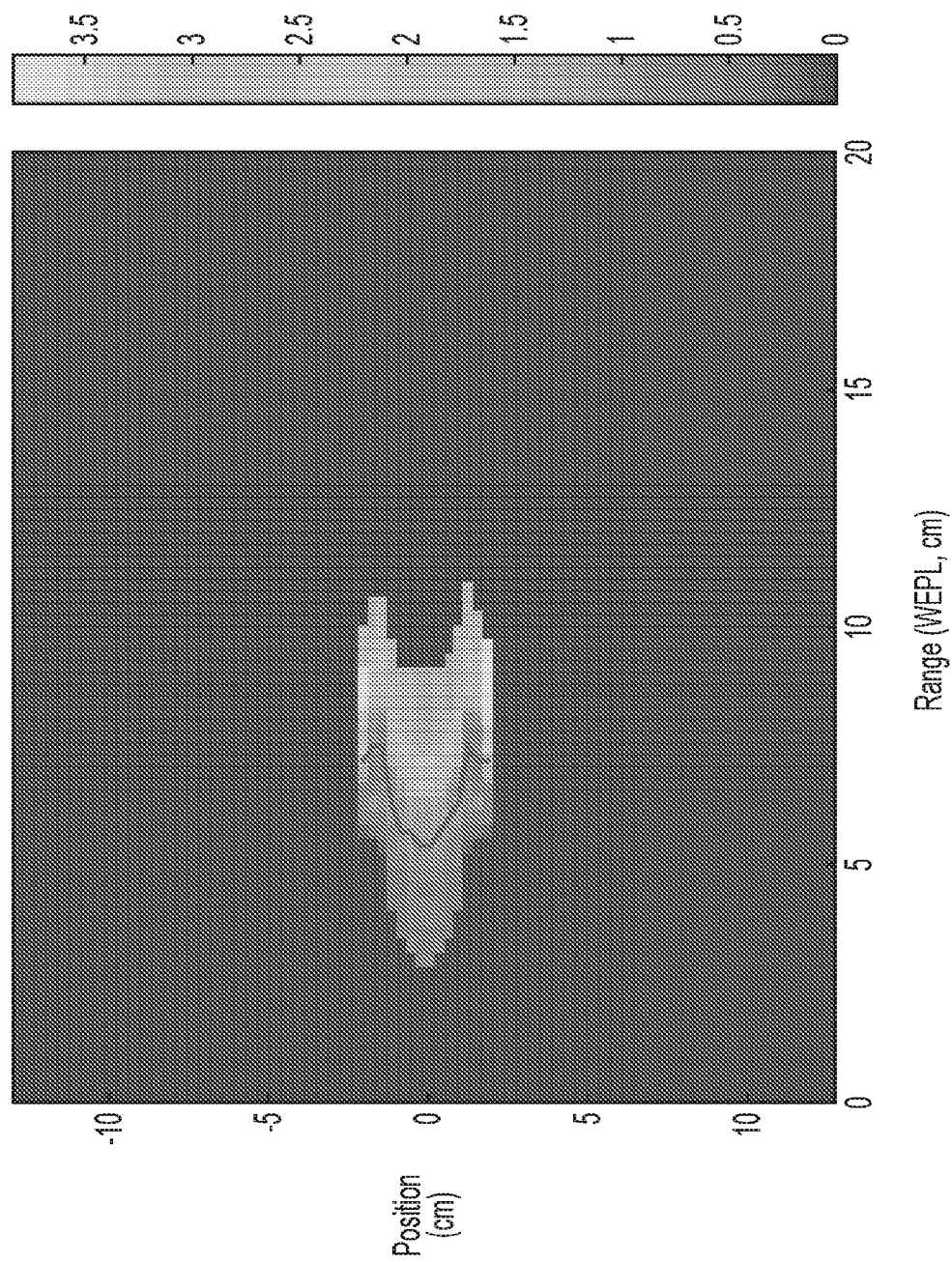
FIG. 6C is another diagram illustrating aspects of an optimized treatment plan.
Figure 6D:
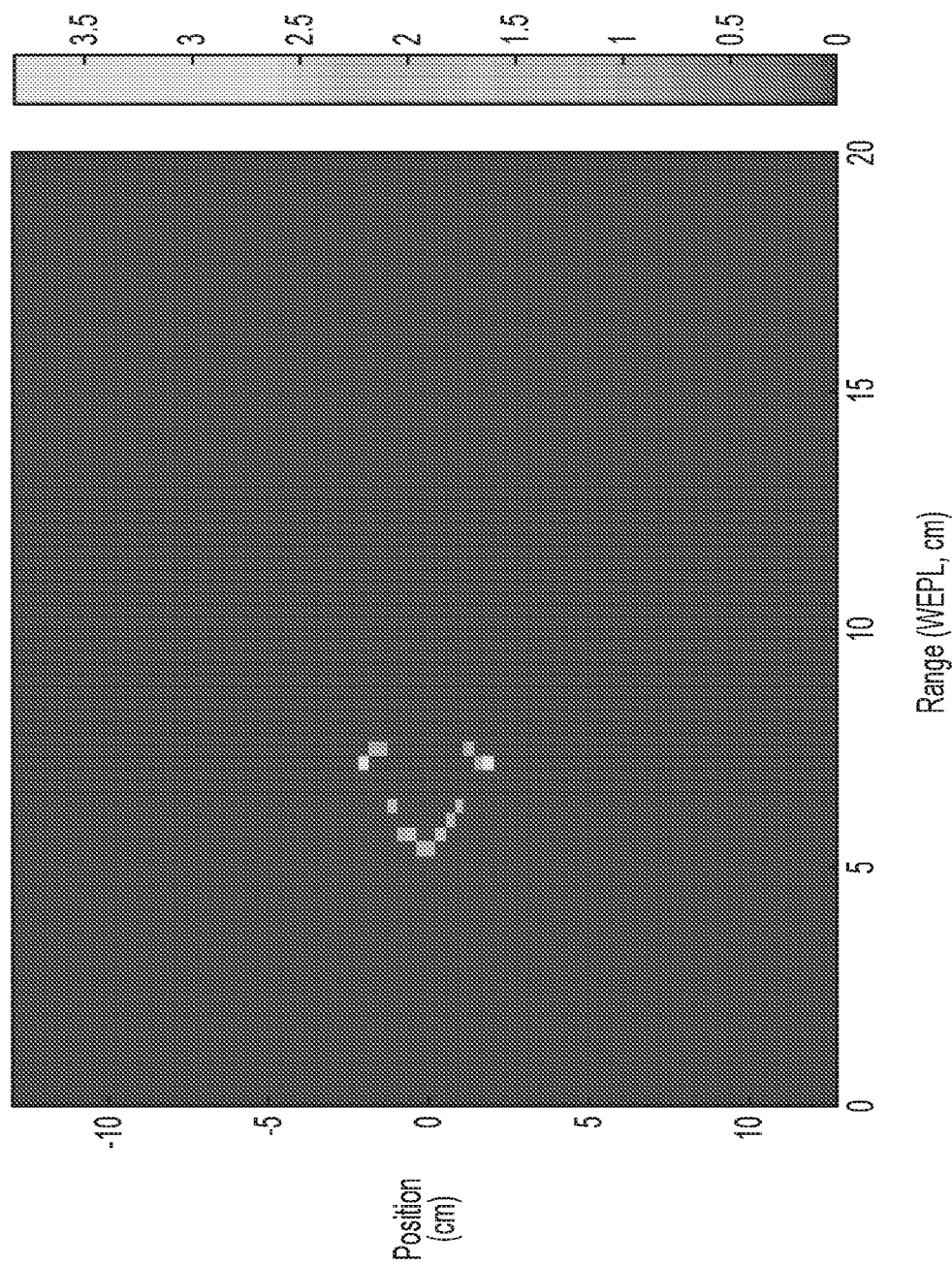
FIG. 6D is another diagram illustrating aspects of an optimized treatment plan.

FIG. 5A shows the first phantom 500 with the crescent target 510, and FIGS. 5B and 5C show the optimized treatment plan. The intensity map overlaid on the phantom image in FIG. 5B indicates the range value for spots in the target, where the small connected circles 540 mark the mid-range spots and were selected as probing beams. FIG. 5C illustrates the spot intensity against the spot position and beam range, and FIG. 5D illustrates the intensity of the probing beam. FIG. 6A illustrates the second phantom 600, which is similar to the first phantom 500 illustrated in FIG. 5A, but the target (or tumor) 620 is a circle and is embraced by the crescent OAR 610. FIG. 6B illustrates the range map overlaid on the phantom image with the mid-range spots 640 marked by the small circles. FIG. 6C illustrates the optimized treatment plan, where the beam shoots from the right side of the second phantom 600. The red curve marks the probing beam which has been distorted (e.g., penetrated deeper into tumor 620) due to the presence of the air pocket 640. FIG. 6D illustrates the intensity map of the probing beam. It is noted that the beams are coming from the left side of the first phantom 500 for FIGS. 5A-5D and from right side of the second phantom 600 for FIGS. 6A-6D, and there is an air pocket on the beam path in both cases.

Figure 7A:
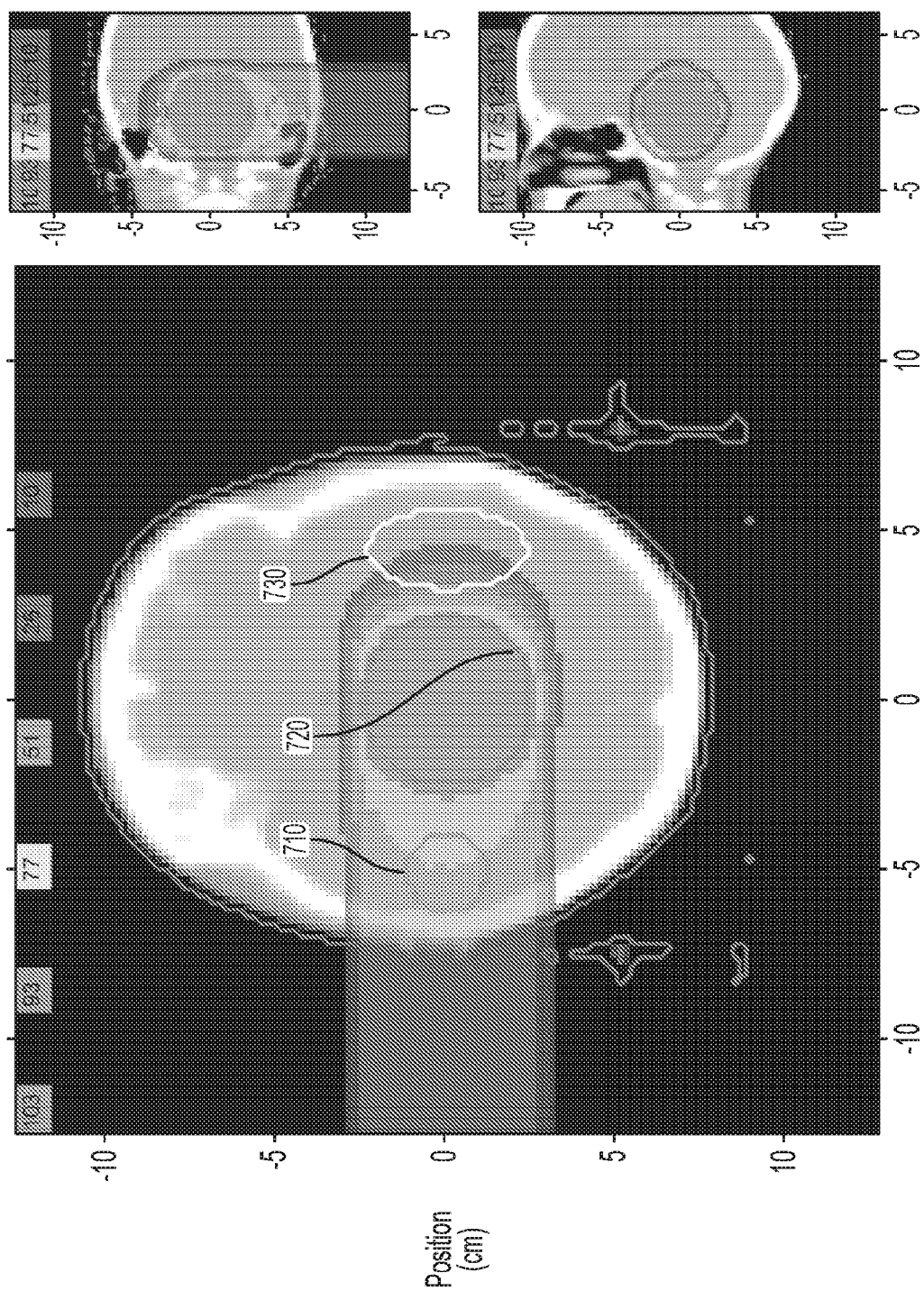
FIG. 7A is a diagram illustrating a transverse view of a CT scan.
Figure 7B:
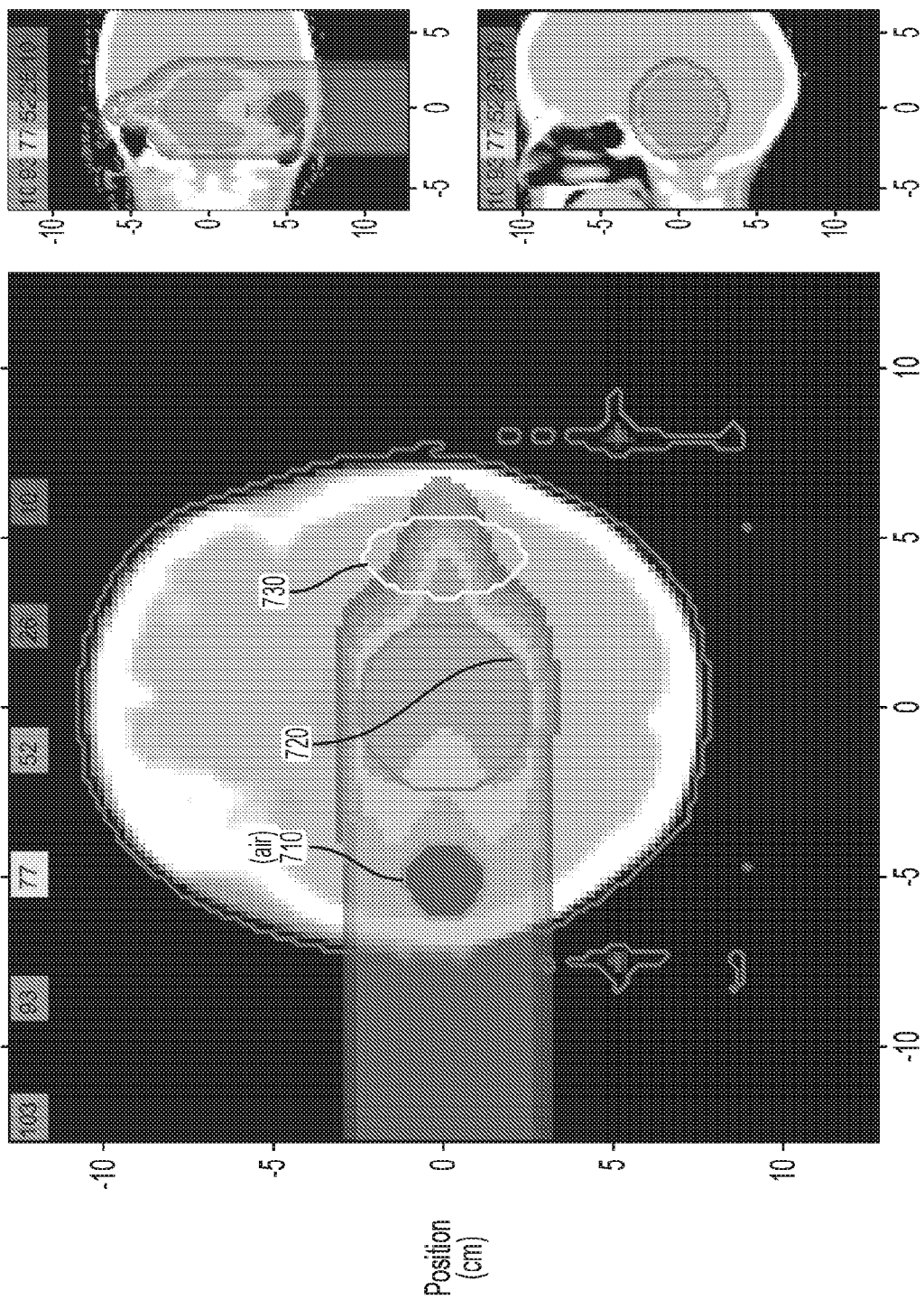
FIG. 7B is a diagram illustrating a coronal view of a CT scan.
Figure 7C:
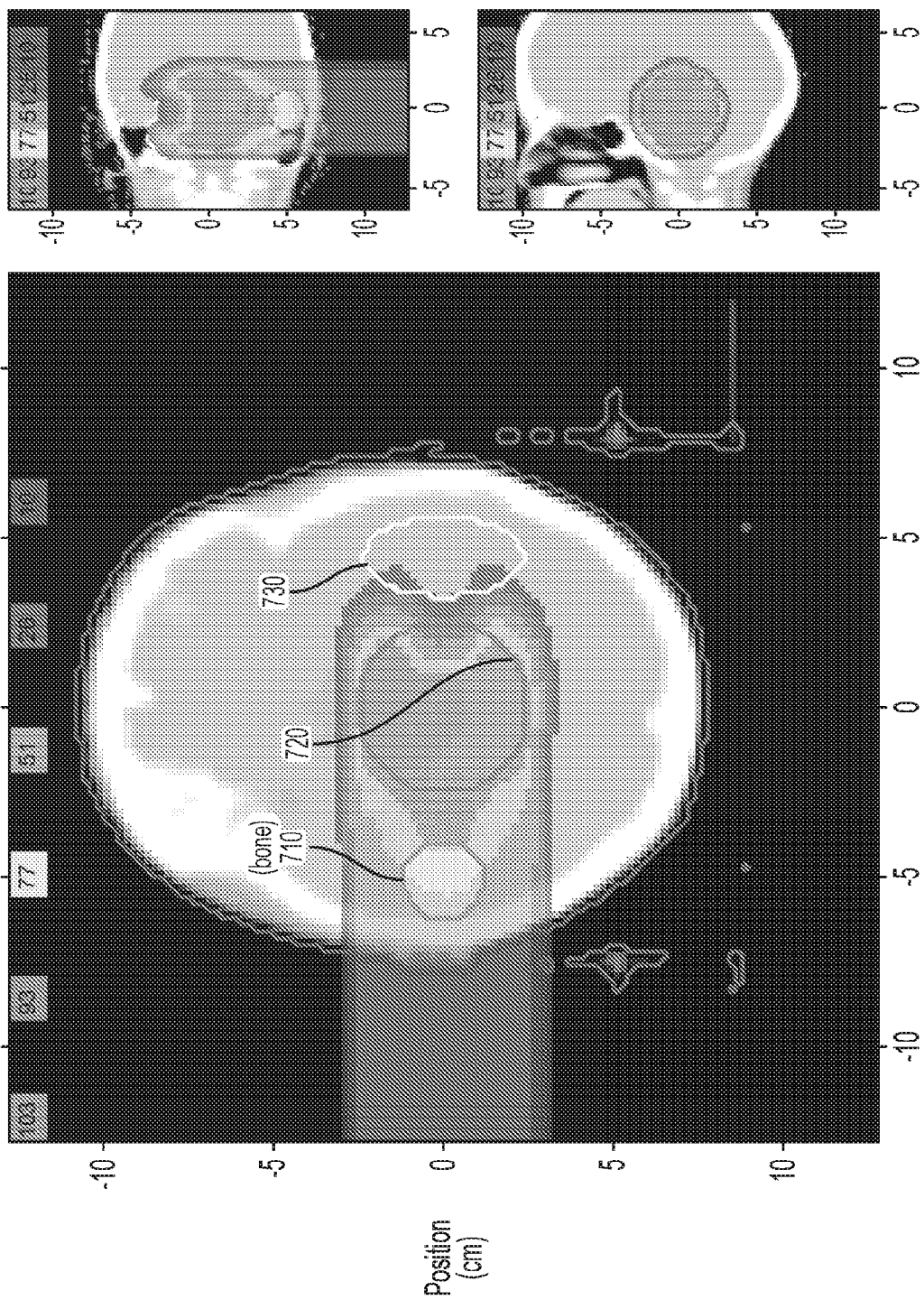
FIG. 7C is a diagram illustrating a sagittal view of a CT scan.

FIGS. 7A-7C show the transverse, coronal, and sagittal (TCS) views of a brain case, respectively. FIG. 7A illustrates an optimized treatment plan and is used as the reference. The three contours (e.g., the three different circles) were the tumor 720, a place holder 710 on the beam path, and an OAR 730, respectively. The beam entered from the left side of the CT. FIGS. 7B and 7C illustrate the delivered dose without modifying the plan when the place holder 710 was filled with air and bone material, respectively. By applying the probing beam strategy and range correction described above, the tests were able to achieve the original plan quality.

Figure 8A:
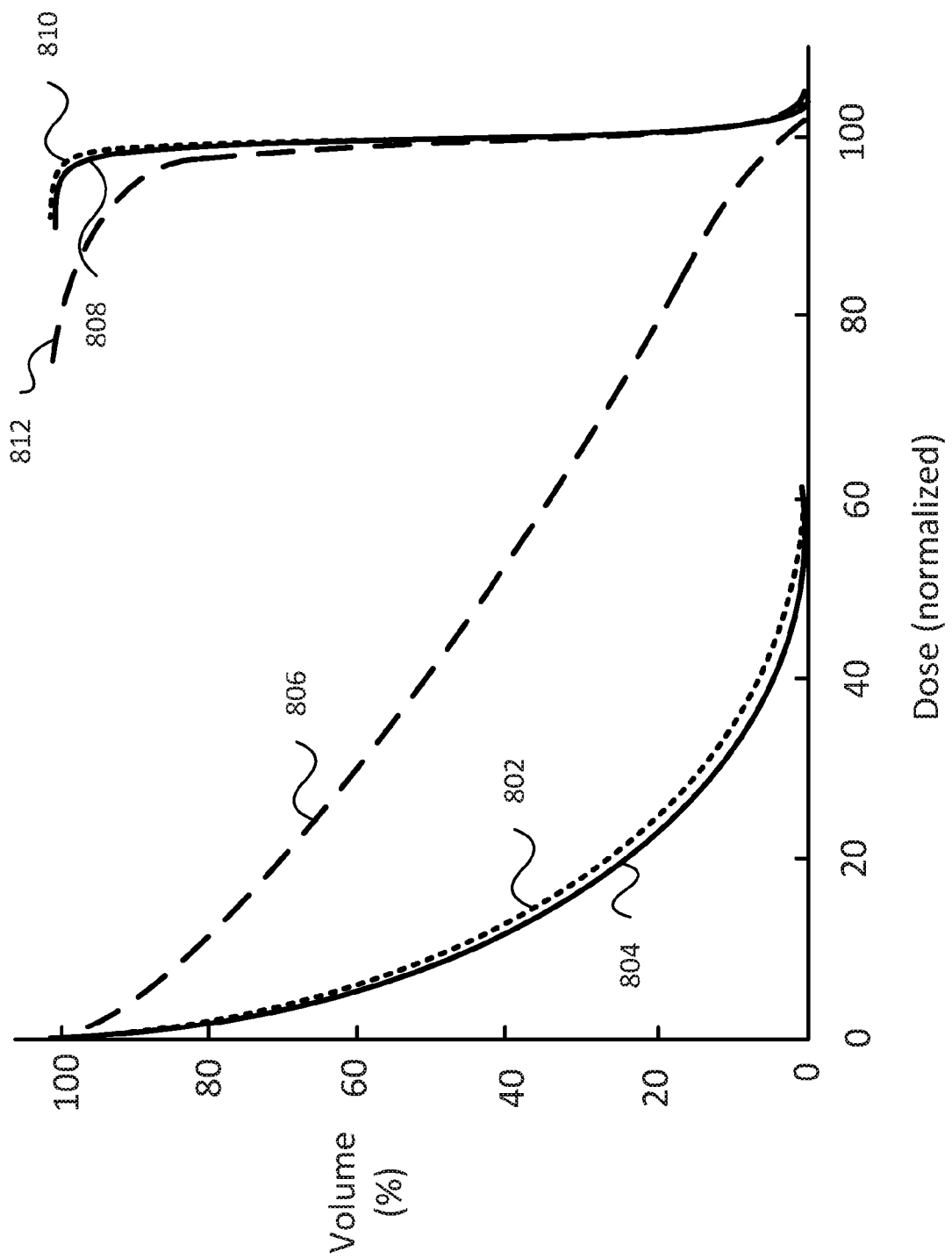
FIG. 8A is a diagram illustrating plots comparing dose volume histograms (DVH) of an original plan, an online delivery, and an adaptive plan.
Figure 8B:
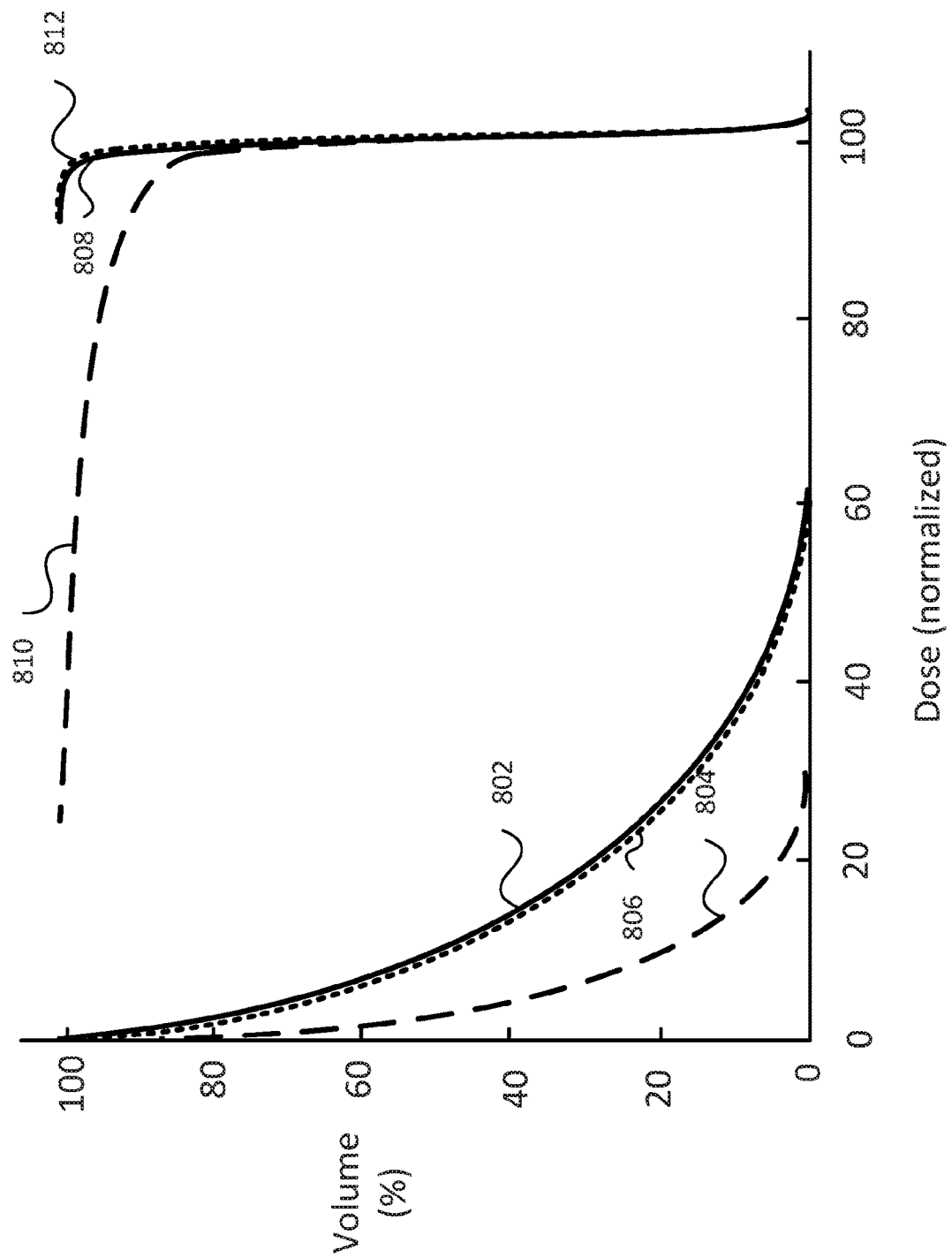
FIG. 8B is another diagram illustrating plots comparing DVH of an original plan, an online delivery, and an adaptive plan.

FIGS. 8A and 8B are plots comparing dose volume histograms (DVH) of an original plan, an online delivery of the unmodified plan, and an adaptive plan, where FIG. 8A illustrates the DVH comparison for a scenario comprising a air-filled place holder, and FIG. 8B illustrates the DVH comparison for a scenario comprising a bone-filled place holder. In FIG. 8A, plots 802, 804, 806 depict DVHs for an OAR according to the original plan (802), the adaptive plan (804) and the online delivery of the unmodified plan (806), and plots 808, 810, 812 depict DVHs for a planning target volume (PTV) according to the original plan (808), the adaptive plan (810), and the online delivery of the unmodified plan (812). In FIG. 8B, plots 802, 804, 806 depict DVHs for an OAR according to the original plan (802), the adaptive plan (804) and the online delivery of the unmodified plan (806), and plots 808, 810, 812 depict DVHs for an planning target volume (PTV) according to the original plan (808), the adaptive plan (810), and the online delivery of the unmodified plan (812). The unmodified plan resulted in under dosage for the tumor in both scenarios. With range correction, it can be seen that the adaptive plan and the original plan were so similar that their DVHs overlap and were indistinguishable. As shown in FIGS. 8A and 8B, the online delivery of the unmodified plan shows worse tumor coverage. With range correction, DVHs of the adaptive plan and the original plan are very similar.

The sharp dose gradient provided by the ion beam is a double-edged sword. It allows much localized dose with minimal tissue damage but is also easily compromised by delivery uncertainty, such as anatomical variations, compared with photon beam therapy. Online range verification is therefore needed to ensure patient safety and treatment quality. The proposed mid-range probing beam strategy of at least those embodiments that utilizes planned treatment spots for online range verification affords multiple advantages. The mid-range probing spots will likely remain inside the tumor even with significant anatomical variation. Additionally, the probing beams are part of the treatment beams, and can be accounted for in subsequent treatment delivery (e.g., following range verification). Therefore, no excess dose is delivered to the patient. Unlike the imaging probing beams (at the dose level of cGy), the therapeutic probing beam (at the dose level of Gy) used in accordance with at least some of the present embodiments may provide 100× stronger signal and therefore much improved image contrast. The Bragg peaks would thus be more easily detectable in a short amount of time, thereby reducing the time required to perform range verification. Additionally, signal contamination due to other decay activities that are increased over time can then be kept minimal, which may be beneficial for online range measurement.

Further, as explained above, by comparing the online detected Bragg peak positions with pre-calculated positions, beam range shifts can be identified and corrected. For range correction, two correction strategies have been proposed: (1) using range-shifted plans and (2) re-optimization using range-shifted beamlets. As demonstrated by the simulations described in the examples above, range shifting to the original plan provides a simple fix to anatomical changes that cannot be addressed by setup alignment. Re-optimization may further take advantages of online anatomical variations. In the simulation studies, range-shifted plans achieved the original plan quality. It is noted that, in the simulations described in the examples above, the plans were generated based on physical dose. If the radiobiological effective (RBE) dose is considered instead of physical dose, then the mid-range spots may have higher intensity. This may results in more probing beam activities and hence would be more advantageous for range detection. It is further noted that the detected range may be used to shift beamlets for re-optimization in the case of tumor shrinkage or a large deformation that requires re-planning.

As shown above, in-vivo online pre-treatment range verification is crucial for particle therapy. The disclosed embodiments provide a range probing technique using mid-range therapeutic beams for online pre-treatment range measurement along with correction strategies for particle therapy. The mid-range therapeutic probing beam techniques of embodiments are safe and practical, and increase in-beam PET detectability compared with the imaging level dose by orders of magnitude without excess radiation to the patient. Further, simulations have demonstrated the feasibility of the proposed strategies and the improvements provided by range-guided online adaptation in accordance with embodiments.

Figure 9:
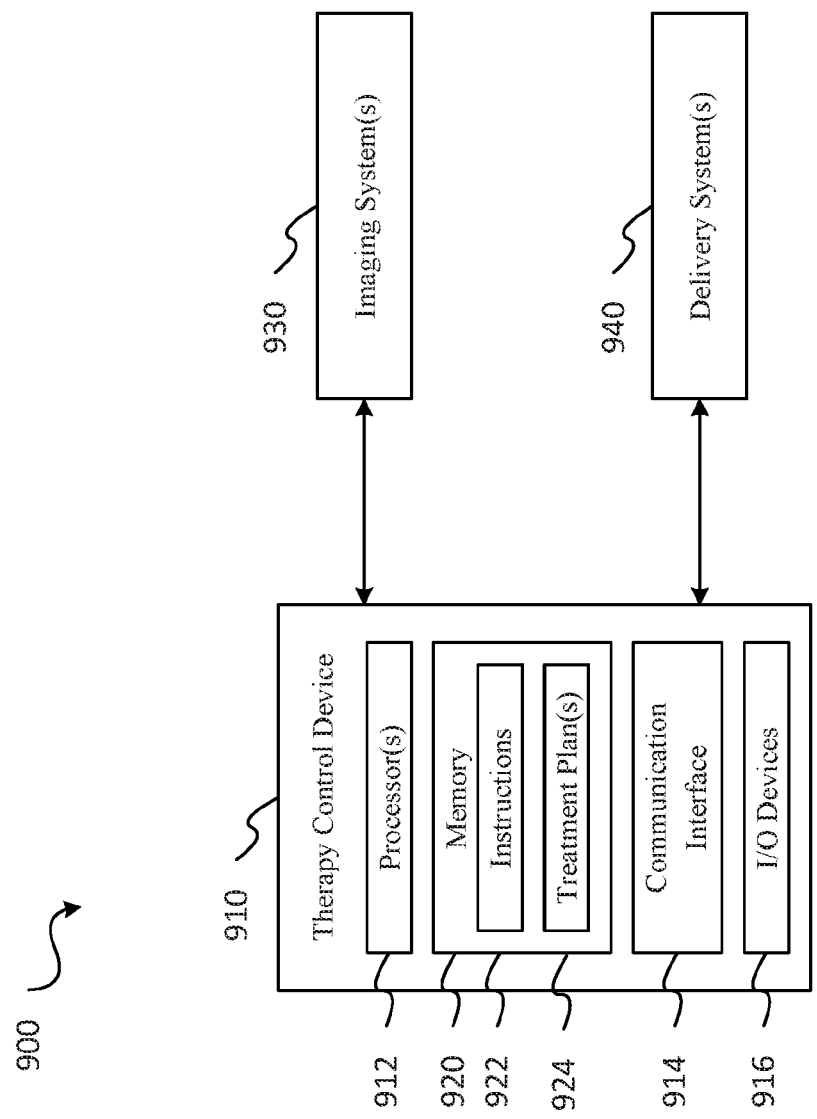
FIG. 9 is a block diagram of a system configured to provide particle therapy in accordance with embodiments.

Referring to FIG. 9, a block diagram of a system configured to provide particle therapy in accordance with embodiments is shown as a system 900. As shown in FIG. 9, the system 900 includes a therapy control device 910, one or more imaging systems 930, and one or more delivery systems 940. In embodiments, the therapy control device 910 may be configured to control operations of, and/or provided information to, the imaging system(s) 930 and/or the delivery system(s) 940 to facilitate particle therapy treatment in accordance with embodiments. For example, the imaging system(s) 930 and/or the delivery system(s) 940 may operate under the control of the therapy control device 910, or may receive information (e.g., a treatment plan, a probing spot plan, and the like) for performing particle therapy operations (e.g., delivering a dose, capturing an image, etc.) from the therapy control device 910.

As shown in FIG. 9, the therapy control device 910 includes one or more processors 912, a communication interface 914, one or more input/output (I/O) devices 916, and a memory 920. The memory 920 may further store instructions 922 and treatment plan data 924. In embodiments, the instructions 922 may be executable by the one or more processors 912 to perform operations for determining/configuring an initial treatment plan, a probing spot plan, modifying the initial treatment plan based on the probing spot plan to determine a final treatment plan, and other operations to facilitate the planning and/or execution of a treatment plan in accordance with embodiments, as described above with reference to FIGS. 1-8B. In embodiments, the instructions 922 may correspond to an application that provides one or more graphical user interfaces that facilitate the development of the treatment plan, the selection of the probing spots, etc. The treatment plan, once developed, may be stored as treatment plan data 924 at the memory 920, and subsequently reviewed and/or modified (e.g., based on the probing spots or for other reasons, such as a change in the patient's physical characteristics or structure). The communication interface 914 may communicatively couple the therapy control device 910 to the imaging system(s) 930 and/or the delivery system(s) 940 via one or more wired or wireless communication links (not shown in FIG. 9). The I/O devices 916 may comprise input devices, such as a mouse, keyboard, touchscreen device, or another device that may be communicatively coupled to the therapy control device 910 to provide instructions, data, and/or other inputs to the therapy control device 910. The I/O devices 916 may further comprise output devices, such a printer, one or more display devices, an audio device (e.g., a speaker(s), a microphone, and the like), other devices, or a combination thereof. In embodiments, the imaging systems may comprise a Positron emission tomography (PET) imaging system, a prompt Gamma imaging system, another imaging system, or a combination thereof. In embodiments, the delivery system(s) 940 may comprise a system configured to deliver proton beams and/or heavy ion beams to facilitate particle therapy treatment of a tumor in accordance with embodiments.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method for probing beam ranges for particle therapy, the method comprising:

determining a configuration of each of one or more probing spots, where each of the one or more probing spots comprises a first dose of radiation delivered prior to performing the particle therapy, where the configuration of each of the one or more probing spots specifies a planned location along a mid-plane of a first interior region of a tumor volume where the first dose of radiation is to be delivered, where the first interior region of the tumor volume is different from a second interior region of the tumor volume proximate an exterior surface of the tumor volume, wherein the second interior region of the tumor volume surrounds the first interior region of the tumor volume, and where the planned location of each of the one or more probing spots is determined such that each of the one or more probing spots is delivered within the tumor volume despite occurrence of a beam shift due to internal body structures of a patient present in a delivery path of a radiation beam;

delivering, via the radiation beam, each of the one or more probing spots to the tumor volume in accordance with the configuration of each of the one or more probing spots;

capturing one or more images of the tumor volume, where the one or more images provide data representative of an actual delivery location of each of the one or more probing spots delivered by the radiation beam;

determining one or more beam shifts based on the one or more images, where each beam shift of the one or more beam shifts corresponds to one probing spot of the one or more probing spots, where each beam shift represents an impact of internal body structures present in the delivery path of the radiation beam on the planned location of the corresponding probing spot, where the internal body structures include bones and air pockets, where first beam shifts associated with a bone present in the delivery path indicate a bone-altered delivery location that is shallower than the planned location of the corresponding probing spot and second beam shifts associated with an air pocket present in the delivery path indicate an air-altered delivery location that is deeper than the planned location of the corresponding probing spot; and configuring delivery locations for the particle therapy based on the one or more beam shifts determined based on the one or more captured images, where the first dose of radiation for each of the one or more probing spots is less than a second dose of radiation delivered during the particle therapy.

2. The method of claim 1, where the one or more probing spots include a plurality of probing spots.

3. The method of claim 1, where determining the one or more beam shifts comprises:

determining an actual delivery location for each of the one or more probing spots based on the one or more images; and comparing the actual delivery location for each of the one or more probing spots to the planned location for each of the one or more probing spots, wherein the one or more beam shifts are determined based on the comparing.

4. The method of claim 3, where the method further comprises determining, for each of the one or more probing spots, a difference between the actual delivery location and the planned location based on the comparing.

5. The method of claim 4, where configuring the delivery locations for the particle therapy based on the delivery locations for each of the one or more probing spots and beam shifts identified based on the one or more captured images comprises modifying a treatment plan based on the difference between the delivery location and the planned location for each of the one or more probing spots.

6. The method of claim 1, where the second dose of radiation provided during the particle therapy has a strength of approximately 2-20 Gy and the first dose of radiation provided by each of the one or more probing spots is less than 1 Gy.

7. The method of claim 1, where the radiation beam is a proton beam.

8. The method of claim 1, where the radiation beam is a heavy ion beam, and where the heavy ion beam is formed using carbon ions, helium ions, or argon ions.

9. The method of claim 1, where the method further comprises:

determining one or more additional configurations for one or more additional probing spots, each of the one or more additional configurations corresponding to an additional angle at which the radiation beam is to be delivered to the tumor volume, where each of the one or more additional probing spots corresponds to an additional planned location within the the tumor volume where an additional first dose of radiation is to be delivered by the radiation beam;

providing the radiation beam to the tumor volume in accordance with each of the one or more additional configurations; and capturing one or more additional images associated with delivery of the one or more additional probing spots to the tumor volume in accordance with each of the one or more additional configurations, where the one or more additional images provide data representative of actual delivery locations for each of the one or more additional probing spots.

10. The method of claim 9, where the method further comprises:

determining the actual delivery locations for each of the one or more additional probing spots; and comparing the actual delivery locations for each of the one or more additional probing spots to the planned locations for each of the one or more additional probing spots.

11. The method of claim 10, where the method further comprises determining, for each of the one or more additional probing spots, a difference between the actual delivery locations and the planned locations based on the comparing.

12. The method of claim 11, where the method further comprises modifying a treatment plan based on the difference between the actual delivery locations and the planned locations for each of the one or more additional probing spots.

13. A non-transitory computer-readable storage medium storing instructions that, when executed by one or more processors, cause the one or more processors to perform operations for probing beam ranges for particle therapy, the operations comprising:

determining a configuration of each of one or more probing spots, where each of the one or more probing spots comprises a first dose of radiation delivered prior to performing the particle therapy, where the configuration of each of the one or more probing spots specifies a planned location along a mid-plane of a first interior region of a tumor volume where the first dose of radiation is to be delivered, where the first interior region of the tumor volume is different from a second interior region of the tumor volume proximate an exterior surface of the tumor volume, wherein the second interior region of the tumor volume surrounds the first interior region of the tumor volume, and where the planned location of each of the one or more probing spots is determined such that each of the one or more probing spots is delivered within the tumor volume despite occurrence of a beam shift due to internal body structures of a patient present in a delivery path of a radiation beam;

delivering, via the radiation beam, each of the one or more probing spots to the tumor volume in accordance with the configuration of each of the one or more probing spots;

capturing one or more images of the tumor volume, where the one or more images provide data representative of an actual delivery location of each of the one or more probing spots delivered by the radiation beam;

determining one or more beam shifts based on the one or more images, where each beam shift of the one or more beam shifts corresponds to one probing spot of the one or more probing spots, where each beam shift represents an impact of internal body structures present in the delivery path of the radiation beam on the planned location of the corresponding probing spot, where the internal body structures include bones and air pockets, where first beam shifts associated with a bone present in the delivery path indicate a bone-altered delivery location that is shallower than the planned location of the corresponding probing spot and second beam shifts associated with an air pocket present in the delivery path indicate an air-altered delivery location that is deeper than the planned location of the corresponding probing spot; and configuring delivery locations for the particle therapy based on the one or more beam shifts determined based on the one or more captured images, where the first dose of radiation for each of the one or more probing spots is less than a second dose of radiation delivered during the particle therapy.

14. The non-transitory computer-readable storage medium of claim 13, where the one or more probing spots include a plurality of probing spots.

15. The non-transitory computer-readable storage medium of claim 13, where the one or more beam shifts are determined by:

determining an actual delivery location for each of the one or more probing spots based on the one or more images; and comparing the actual delivery location for each of the one or more probing spots to the planned location for each of the one or more probing spots, wherein the one or more beam shifts are determined based on the comparing.

16. A system for probing beam ranges for particle therapy, the system comprising:

a memory; and one or more processors coupled to the memory, the one or more processors configured to:

determine a configuration of each of one or more probing spots, where each of the one or more probing spots comprises a first dose of radiation delivered prior to performing the particle therapy, where the configuration of each of the one or more probing spots specifies a planned location along a mid-plane of a first interior region of a tumor volume where the first dose of radiation is to be delivered, where the first interior region of the tumor volume is different from a second interior region of the tumor volume proximate an exterior surface of the tumor volume, wherein the second interior region of the tumor volume surrounds the first interior region of the tumor volume, and where the planned location of each of the one or more probing spots is determined such that each of the one or more probing spots is delivered within the tumor volume despite occurrence of a beam shift due to internal body structures of a patient present in a delivery path of a radiation beam;

deliver, via the radiation beam, each of the one or more probing spots to the tumor volume in accordance with the configuration of each of the one or more probing spots;

capture one or more images of the tumor volume, where the one or more images provide data representative of an actual delivery location of each of the one or more probing spots delivered by the radiation beam;

determine one or more beam shifts based on the one or more images, where each beam shift of the one or more beam shifts corresponds to one probing spot of the one or more probing spots, where each beam shift represents an impact of internal body structures present in the delivery path of the radiation beam on the planned location of the corresponding probing spot, where the internal body structures include bones and air pockets, where first beam shifts associated with a bone present in the delivery path indicate a bone-altered delivery location that is shallower than the planned location of the corresponding probing spot and second beam shifts associated with an air pocket present in the delivery path indicate an air-altered delivery location that is deeper than the planned location of the corresponding probing spot; and configure delivery locations for the particle therapy based on the one or more beam shifts determined based on the one or more captured images, where the first dose of radiation for each of the one or more probing spots is less than a second dose of radiation delivered during the particle therapy.

17. The system of claim 16, where the one or more processors are configured to:

determine one or more additional configurations for one or more additional probing spots, each of the one or more additional configurations corresponding to an additional angle at which the radiation beam is to be delivered to the tumor volume, where each of the one or more additional probing spots corresponds to an additional planned location within the interior of the tumor volume where an additional first dose of radiation is to be delivered by the radiation beam;

deliver, via the radiation beam, the one or more additional probing spots to the tumor volume in accordance with each of the one or more additional configurations; and capture one or more additional images associated with delivery of the one or more additional probing spots to the tumor volume in accordance with each of the one or more additional configurations, where the one or more additional images provide data representative of actual delivery locations for each of the one or more additional probing spots.

* * * * *